(12) United States Patent
    Pollack

(10) Patent No.: US 11,324,907 B1
(45) Date of Patent: *May 10, 2022

(54) TRACHEOTOMY DEVICE AND METHOD OF USE

(71) Applicant: Joshua D. Pollack, Short Hills, NJ (US)

(72) Inventor: Joshua D. Pollack, Short Hills, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/487,173

(22) Filed: Sep. 28, 2021

Related U.S. Application Data

(63) Continuation of application No. 17/182,505, filed on Feb. 23, 2021, now Pat. No. 11,129,952.

(51) Int. Cl.
    *A61M 16/04* (2006.01)
    *A61M 16/00* (2006.01)

(52) U.S. Cl.
    CPC ..... *A61M 16/0472* (2013.01); *A61M 16/0434* (2013.01); *A61M 2016/0027* (2013.01); *A61M 2205/3576* (2013.01); *A61M 2205/52* (2013.01); *A61M 2205/581* (2013.01); *A61M 2205/583* (2013.01); *A61M 2205/8206* (2013.01)

(58) Field of Classification Search
    CPC .. A61M 16/00; A61M 16/04; A61M 16/0402; A61M 16/0429; A61M 16/0465; A61M 16/0472; A61M 16/0488; A61M 2016/0027; A61M 2205/3576; A61M 2205/52; A61M 2205/581; A61M 2205/583; A61M 2205/8206; A61B 17/3476

See application file for complete search history.

(56) References Cited

U.S. PATENT DOCUMENTS

| 4,438,768 A * | 3/1984 | Barrickman ...... A61M 16/0472 128/207.29 |
| 4,556,059 A | 12/1985 | Adamson, Jr. |
| 11,129,952 B1 * | 9/2021 | Pollack ............. A61M 16/0472 |
| 2012/0211006 A1 * | 8/2012 | Gill ........................ A61B 34/30 128/200.26 |
| 2015/0150642 A1 * | 6/2015 | Lau ..................... A61B 17/3476 606/108 |
| 2020/0179631 A1 * | 6/2020 | Sarkar .................. A61B 5/1077 |
| 2021/0045711 A1 * | 2/2021 | Brattain ............... A61B 8/4416 |

FOREIGN PATENT DOCUMENTS

GB 2423717 A * 9/2006 ........ A61M 16/0472

* cited by examiner

*Primary Examiner* — Joseph D. Boecker
(74) *Attorney, Agent, or Firm* — Kelley Drye & Warren LLP

(57) ABSTRACT

A device for performing a tracheotomy on a patient without the assistance of a medical professional. The device may include one or more mechanical arms that cause a blade to create an incision, cause a dilating tool to dilate the incision, and cause a tracheotomy tube to be inserted into the incision. The device may further include a scanner and/or a hollow needle connected to an air pressure sensor that may be used to detect whether the device is aligned with the patient's airway.

17 Claims, 11 Drawing Sheets

TRACHEOTOMY DEVICE AND METHOD OF USE

CROSS-REFERENCE TO RELATED APPLICATIONS

This application is a continuation of U.S. patent application Ser. No. 17/182,505, filed on Feb. 23, 2021. The entire contents of that application are incorporated herein by reference.

BACKGROUND OF THE INVENTION

A tracheotomy is a surgical procedure in which an incision (a "tracheostomy") is made in the front of the neck, opening a direct airway (hole or stoma) in the trachea (windpipe). A breathing tube (a "tracheotomy tube") is placed through the incision and into the trachea to keep the incision open for breathing. After a tracheotomy procedure is completed, breathing is done through the tracheotomy tube rather than through the nose and mouth.

A tracheotomy may be performed for a variety of reasons, including: (1) emergency airway access, (2) airway access for prolonged mechanical ventilation, (3) functional or mechanical upper airway obstruction (e.g., obstruction caused by choking on food or other object), or (4) decreased/incompetent clearance of tracheobronchial secretions. In the case of an emergency such as a traumatic injury to the face or neck, a person's airway may be suddenly blocked by swelling or blood. A tracheotomy may need to be done quickly to re-establish the airway. A tracheotomy may also be performed to address acute angioedema and inflammation of the head and neck.

A tracheotomy tube may include a cuff, an inflatable balloon at the end of the tube, to secure the tracheotomy tube in place, and to prevent air from leaking out. A cuff may also help prevent saliva and other secretions and swallowed liquids from traveling to the lungs.

Although the airway of most persons is aligned with the center of their neck, the airway may be located off-center. Accordingly, locating the airway is typically performed before an incision is made. Once the airway is located, a transverse (horizontal) incision may be made above the suprasternal notch, or a vertical incision may be made in the midline of the neck from the thyroid cartilage to just above the suprasternal notch.

Skin, subcutaneous tissue, and strap muscles may be retracted aside to expose the thyroid isthmus, which can be cut or retracted upwards. The trachea may be cut open, either through the space between cartilage rings or vertically across multiple rings. Once the incision is made, a properly sized tube is inserted. The tracheotomy apparatus may then be attached to the neck with, for example, tracheotomy ties and/or skin sutures.

However, a person may require a tracheotomy when a medical professional is not available to perform the surgical procedure. For example, a person choking in a restaurant who does not respond to other measures, such as the Heimlich maneuver, may suffocate from the blockage in their throat if a tracheotomy is not performed. As another example, military personnel during wartime deployment may suffer an injury requiring a tracheotomy, but may not have access to a medical professional who can perform the procedure.

There is therefore a need for a device and methods that can be used to perform a tracheotomy in an emergency when a medical professional is not available to perform the procedure.

SUMMARY OF THE INVENTION

The present invention is directed to a device capable of performing a tracheotomy procedure.

It is an object of the present invention to provide a portable device that may be used to perform a tracheotomy procedure without the assistance of a medical professional.

It is a further object of the present invention to provide a portable device capable of causing the tracheotomy tube to be aligned with the airway in which the tracheotomy tube is to be inserted. Alignment may be achieved by matching the shape or contour of the front wall of the device, or an indentation in the front wall of the device, with the outer surface of the throat in which the tracheotomy tube is to be inserted. Additionally or alternatively, the device may include a hollow needle that may be inserted into the throat and used to detect the location of the airway. For example, an air pressure sensor connected to the needle may be used to sense a change in air pressure, indicating that the needle has penetrated the airway. For example, the air pressure sensor may be electronic communication with the controller, and data from the air pressure sensor may be transmitted to the controller. The controller may then determine whether data from the air pressure sensor indicates a change in pressure. If no change in air pressure is detected, or if a change in air pressure is detected but below a predetermine amount or predetermined percentage change, the needle may be repositioned one or more time until the airway is penetrated and a change in air pressure (or change in pressure above a predetermined amount or predetermined percentage) is detected.

A device in accordance with the present invention may include one or more mechanical arms that may be used to create an incision in a patient's neck with a blade, dilate the incision with a dilating tool, and/or insert a tracheotomy tube into the incision.

Numerous variations may be practiced in the preferred embodiment.

BRIEF DESCRIPTION OF THE DRAWINGS

A further understanding of the invention can be obtained by reference to exemplary embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

DETAILED DESCRIPTION OF THE INVENTION

Figure 1:
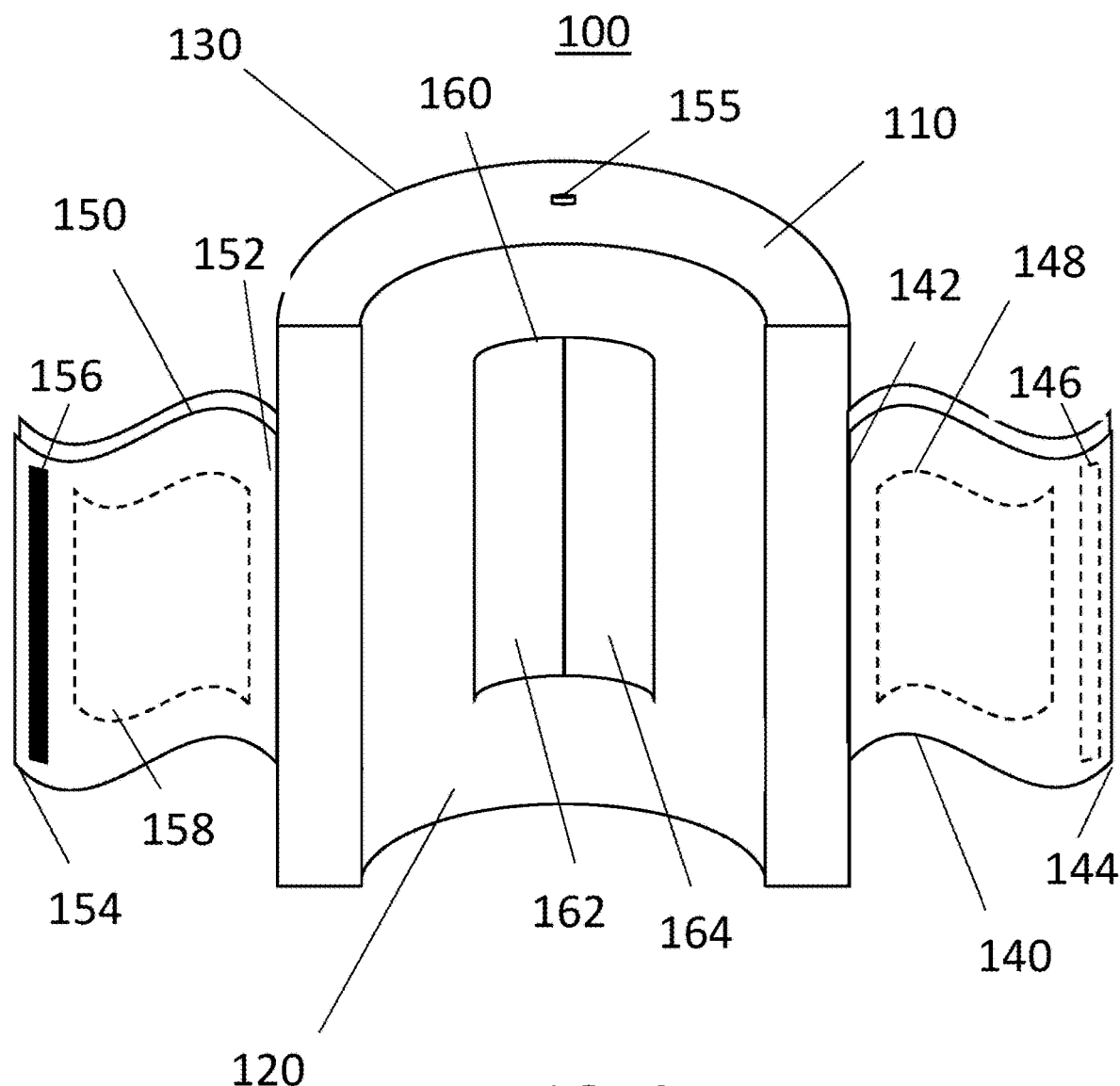
FIG. 1 depicts an exemplary device in accordance with the present invention.

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiments for purposes of disclosure and to provide a basis for the claims herein, which define the scope of the invention. It should also be noted that, as used in the specification and the appended claims, the singular forms "a", "an", and "the" include plural referents unless the context clearly indicates otherwise.

Use of the term "exemplary" means illustrative or by way of example, and any reference herein to "the invention" is not intended to restrict or limit the invention to the exact features or steps of any one or more of the exemplary embodiments disclosed in the present specification. Also, repeated use of the phrase "in one embodiment," "in an exemplary embodiment," or similar phrases do not necessarily refer to the same embodiment, although they may. It is also noted that terms like "preferably," "commonly," and "typically," are not used herein to limit the scope of the claimed invention or to imply that certain features are critical, essential, or even important to the structure or function of the claimed invention. Rather, those terms are merely intended to highlight alternative or additional features that may or may not be used in a particular embodiment of the present invention.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described.

The terms "patient" and "user" as recited herein refer to a person on whom the methods disclosed herein are performed and/or a person on whom the devices disclosed herein are used. The term "patient" is not intended to be limited to a person under the care of a medical professional or a person treated in a hospital, doctor's office, or any other medical care facility.

FIG. 1 depicts an exemplary portable tracheotomy device (100) in accordance with the present invention. Portable tracheotomy device (100) includes a housing (110). Housing (110) may have a front wall (120) and a back wall (130). Front wall (120) and/or back wall (130) may be curved so as to follow the contour of a person's neck.

Attached to housing (110) may be one or more attaching elements (140, 150). Each attaching element (140, 150) may be a strap extend from a first edge (142, 152) attached to housing (110), to a second edge (144, 154). Attaching elements (140, 150) may be capable of wrapping around a person's neck so that second end (142) of first attaching element (140) and second end (152) of second attaching element (150) may be joined together behind the person's neck. One or both of the second ends (142, 152) may have one or more joining elements (146, 156), such as one or more strips of hook and loop material, an adhesive, one or more snaps, and/or one or more clips that may be used to connect or releasably join the second ends (142, 152) together.

Figure 2:
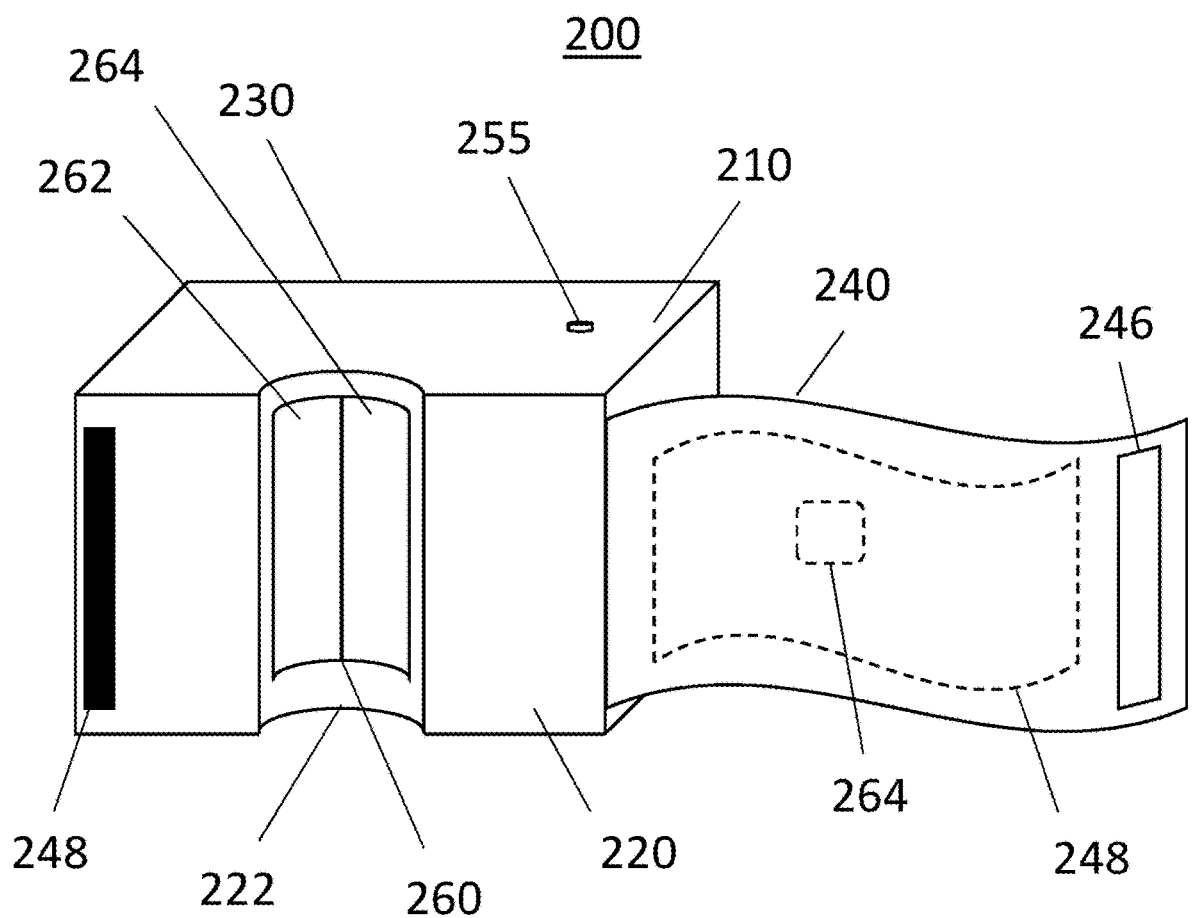
FIG. 2 depicts an exemplary device in accordance with the present invention.

FIG. 2 shows an alternative embodiment of a portable tracheotomy device (200) having housing (210). Housing (210) of portable tracheotomy device (200) has a front wall (220) and back wall (230). Front wall (220) of portable tracheotomy device (200) includes an indentation (222) that may follow the curvature of a person's throat.

Attached to housing (210) may be one or more attaching elements (240), such as a strap, that may be of sufficiently length to wrap around a person's neck. Each attaching (240) element may extending from a first end (242) attached to housing (210) to a second end (244). One or more joining elements (246), such as one or more strips of hook and loop material, an adhesive, one or more snaps, and/or one or more clips, located at or near second end (244) of each attaching element (240) may connect to one or more complementary joining elements (248) attached to housing (210).

Each attaching element (140, 150, 240) may have an airtight chamber (148, 158, 248) that may be inflated. Inflating each airtight chamber (148, 158, 248) may help position the portable tracheotomy device (100, 200) relative to a patient's neck, may help position the head of a patient (e.g., may cause a patient's head to tilt backward, may cause a patient's head to face forward), and/or may help immobilize a patient's neck in case the patient has suffered a spinal injury. One or more air canisters (not shown) located inside or outside housing (110, 210) may be connected to each airtight chamber (148, 158, 248) by, for example, a tube or needle. Air may then be forced from each air canister into each airtight chamber (148, 158, 248), causing each airtight chamber (148, 158, 248) to inflate. The amount of air in each air canister may be limited so to prevent the airtight chambers (148, 158, 248) from over-inflating or bursting that may result from receiving too much air. Additionally or alternatively, an air pressure sensor may be attached to the air canisters and each airtight chamber (148, 158, 248) and may cause the air canisters to stop injecting air into the airtight chambers (148, 158, 248) when the pressure in the airtight chambers (148, 158, 248) reaches a predetermined level.

Alternatively, each airtight chamber (148, 158, 248) may be inflated using a chemical reaction. For example, each airtight chamber (148, 158, 248) may contain a first chemical and a packet (shown as 264 in FIG. 2). Within the packet (264) may be a second chemical. The first and second chemicals may be chosen from common chemicals known to quickly generate a gas when they come in contact with each other, such as the chemicals commonly used to inflate airbags. Packet (264) may be formed from a thin film plastic. Attaching element (240) may be twisted or bent so as to cause packet (264) within airtight chamber (148, 158, 248) to break. When packet (264) is broken, the second chemical within packet (264) comes into contact with first chemical, causing the generation of a gas that may inflate airtight chamber (148, 158, 248).

As shown in FIGS. 1 and 2, front wall of housing (110, 210) may include an aperture (160, 260). One or more doors (162, 164, 262, 264) may cover aperture (160, 260) before tracheotomy device (100, 200) is used. When tracheotomy device (100, 200) is used to perform a tracheotomy procedure, the one or more doors (162, 164, 262, 264) may be opened by hand. Alternatively, a motor (not shown) may be used to open the doors. The motor may be activated by, for example, a button (155, 255) located on housing (110, 210). Additionally or alternatively, button (155, 255) may cause the device to perform the other functions disclosed below.

Figure 3A:
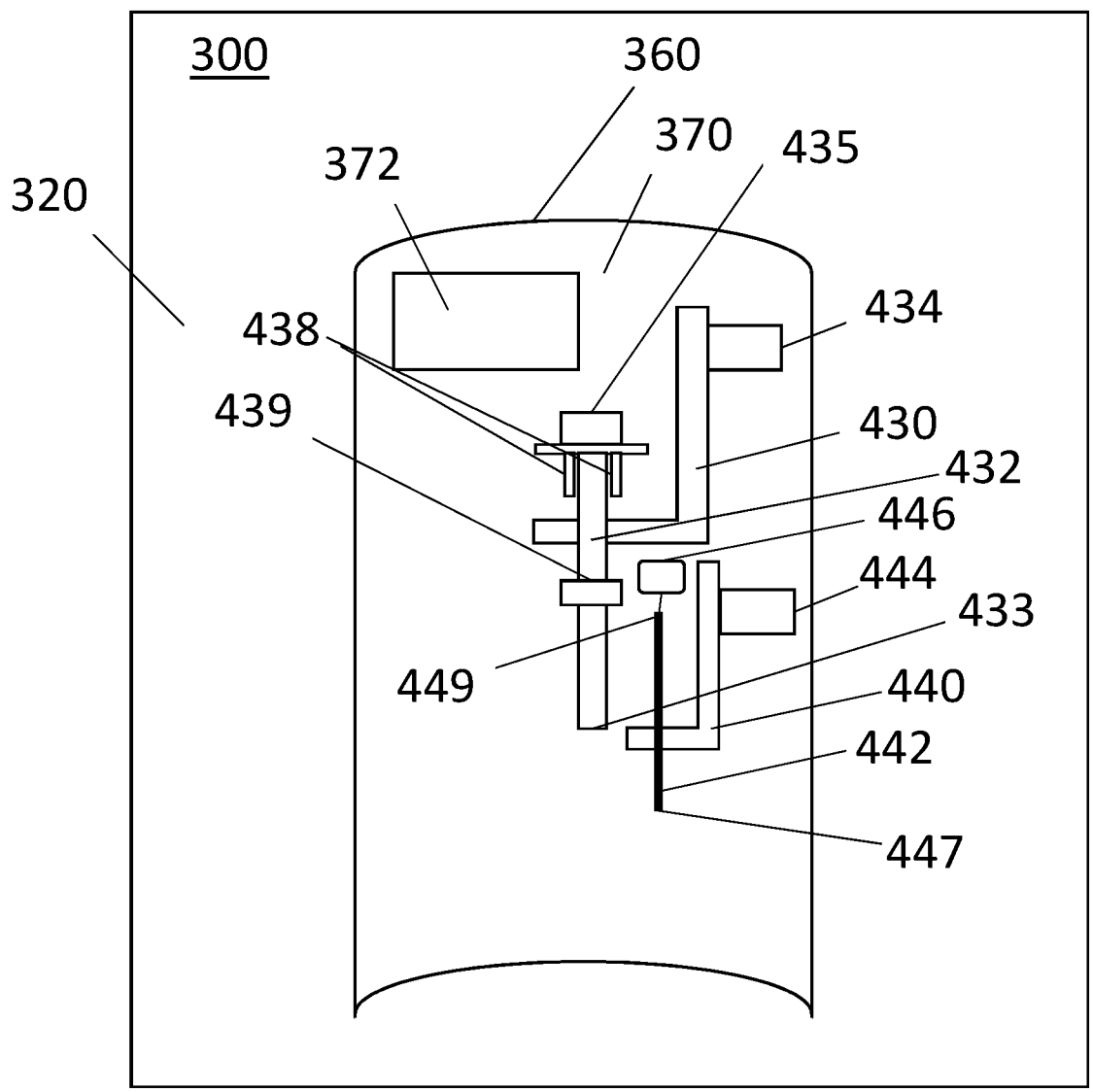
FIG. 3A depicts an interior region of an exemplary device in accordance with the present invention.

The aperture (160, 260) in front wall (120, 220) of housing (110, 210) may lead to an interior region of housing (110, 210) between front wall (120, 220) and back wall (130, 230). FIG. 3 shows an aperture (360) in front wall (320) of a device (300) in accordance with the present invention. Aperture (360) leads to interior region (370). Located within interior region (370) may be components that may perform the tracheotomy procedure. For example, within interior region (370) may be a power source (372) such as a battery, a non-transitory memory (not shown) having a machine-readable medium comprising machine executable code, and one or more processors or controllers (not shown) coupled to the memory. Back wall (130, 230) of housing (110, 210) and/or any other walls of housing (110, 210) may have one or more apertures (not shown) in fluid communication with interior region (370) to allow air to be exchanged between interior region (370) and the surrounding area.

To orient device (100, 200) on the neck of a patient so that the incision may be made at a location where it leads to the patient's airway, the inner wall (120) and/or indentation (222) on inner wall (220) of device (100, 200) may be aligned with the front of a patient's throat before the tracheotomy procedure is performed. As noted above, most patients' airways are aligned at the center of the neck, between the left and right side.

Alternatively, device (100, 200) may include one or more components that may be used to ensure that device (100, 200) is properly aligned, preferably before an incision is made. For example, device (100, 200) may include a scanner, such as an ultrasound scanner, that can scan for the presence or absence of tissue across a cross-section of a patient's neck. Based on data received from the scanner, the processor or controller may use a machine learning algorithm to predict whether device (100, 200) is aligned so that an incision at a particular location relative to the device would lead to the patient's airway. If the machine learning algorithm returns a result below a predetermined threshold used to assess whether device (100, 200) is properly aligned on the patient's neck, device (100, 200) may emit or transmit a signal, such as an audible or visual signal, indicating that device (100, 200) is not properly aligned. For example, a sound generating device (not shown) such as a speaker or a bell may signal that the device is not properly aligned, by emitting a spoken message or by sounding a sound such as a chime. Alternatively, a display screen (not shown) or a light (not shown) on device (100, 200) may emit a signal indicating whether device (100, 200) is or is not properly aligned. If device (100, 200) emits or transmits a signal indicating that it is not properly aligned, device (100, 200) may be re-oriented on the patient's neck before the tracheotomy procedure is performed.

Additionally or alternatively, device (100, 200) may include other means for detecting whether device (100, 200) is aligned with a patient's airway. For example, referring to FIG. 3A, within interior region (370) may be a an open-tip hollow needle (442), extending longitudinally from a pointed, open tip at a first end to a second end. The open-tip hollow needle (442) may be, for example, attached to a first mechanical arm (440) which may be attached to a first motor (444) powered by the power source (370) and configured to move the first mechanical arm (440). A first driver (not shown) may be connected to, and configured to drive, the first motor (444). Also within interior region (370) may be an air pressure sensor (446) in fluid communication with the interior of hollow needle (442) and in electronic communication with the controller.

The device may be configured to extend first end of hollow needle (442) a predetermined distance outside housing (110, 210) at a first location. The air pressure sensor (446) in fluid communication with the interior of hollow needle (442) may be used to detect a change in air pressure after hollow needle (442) is extended a predetermined distance (e.g., a distance representing at least the distance at which first end (447) of hollow needle (442) would pierce the skin of the patient). Data collected from the air pressure sensor (446) may be used (e.g., by the controller) to determine whether there is a change in air pressure in hollow needle (442) above a predetermined amount, above a predetermined percentage, or within a predetermined range, indicating hollow needle (442) has been inserted into the patient's airway. If a change in air pressure above a predetermined amount or percentage, or within a predetermined range, is detected, device (100, 200) may be configured to proceed with the tracheotomy procedure at the first location of the patient's neck.

If an airway is not detected (e.g., if data from the air pressure sensor (446) does not indicate a change in air pressure above a predetermined amount or within a predetermined range, therefore indicating that hollow needle (442) has not been inserted into the patient's airway), the device may be configured to retract the hollow needle (442) from the patient's neck, move hollow needle (442) to a second location relative to the first location on the patient's neck, and extend hollow needle (442) a predetermined distance outside housing (110, 210) at the second location. The second location may be a predetermined distance (e.g., 5 millimeters or one centimeter) and in a predetermined direction (e.g., right, left, up or down) relative to the first location. Once hollow needled (442) is extended at the second location, data collected from the air pressure sensor (446) may again be used by the controller to determine whether hollow needle (442) has been inserted into the patient's airway. If an airway is detected, the tracheotomy procedure may proceed at the second location. If an airway is not detected, the steps of moving hollow needle (442) to a different location, reinserting hollow needle (442), and detecting whether hollow needle (442) has been inserted into the patient's airway may be repeated until the airway is detected. The repetition of those steps may be limited to a predetermined number of time, such as five times.

Once the procedure proceeds, one or more tools within interior region (370) may be used to create an incision in a patient's neck, dilate the incision, and/or insert a tracheotomy tube. For example, referring again to FIG. 3A, within interior region (370) may be a second mechanical arm (430), a tracheotomy tube (432) attached to second mechanical arm (430), and a second motor (434) powered by power source (370) and configured to move second mechanical arm (430). Also within interior region (370) may be a second driver (not shown), configured to drive second motor (434). Tracheotomy tube (432) may extend from a first end (433) to a second end (435). First end (433) of tracheotomy tube (432) may be tapered. Tracheotomy tube (432) may include flanges (438) that may extend outward once the tracheotomy tube (432) is inserted into the incision, preventing the tracheotomy tube (432) from inadvertently sliding out of the incision. Tracheotomy tube (432) may also include an inflatable cuff (439) commonly found on tracheotomy tubes. Inflatable cuff (439) may be inflated to secure tracheotomy tube (432) in place.

Device (100, 200) may be configured to extend tracheotomy tube (432) through aperture (160, 260), outside housing (110, 210), and toward the patient's neck. First end (433) of tracheotomy tube (432) may be sharp, rigid, and/or tapered to help the tracheotomy tube (432) to penetrate into the patient's neck until first end (433) reaches the patient's airway. First end (433) may have a cross-section in the shape of a circle, and device (100, 200) may rotate tracheotomy tube (432) about an axis extending through the center of, and orthogonal to, that circular cross-section as it is penetrating the patient's neck to help facilitate insertion of tracheotomy tube (432). Tracheotomy tube (432) may be rotated in one direction (clockwise or counter clockwise), or tracheotomy tube (432) may be rotated in one direction and then in the reverse direction once or a plurality of times.

Figure 3B:
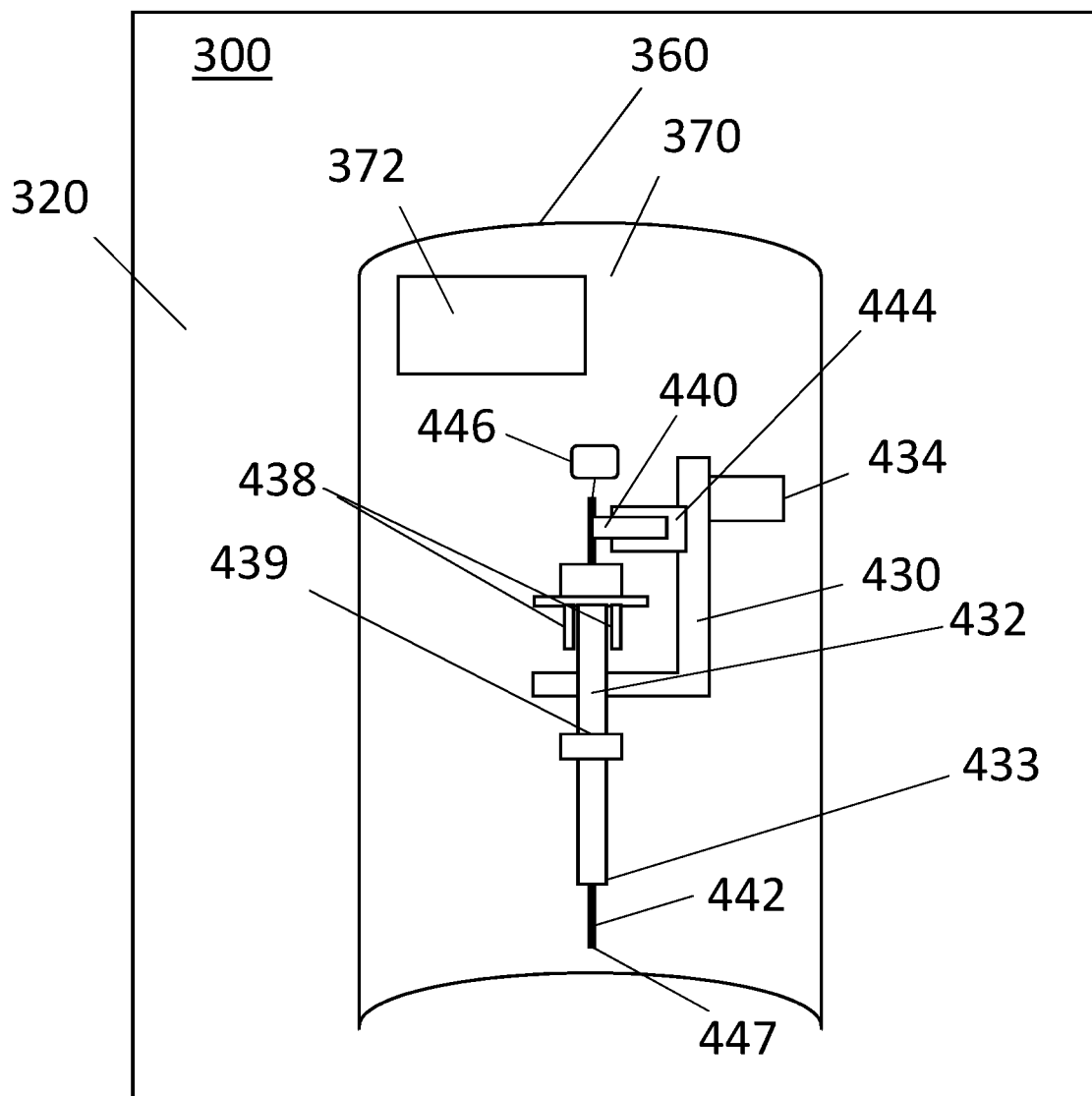
FIG. 3B depicts an interior region of an exemplary device in accordance with the present invention.

Hollow needle (442) may be removed from the patient's neck before tracheotomy tube (432) is inserted. Alternatively, hollow needle (442) may remain inserted in the patient's neck while tracheotomy tube (432) is inserted, and thereby used as a guide for inserting tracheotomy tube (432) into the patient's airway. For example, if hollow needle (442) remains in the patient's neck, it may act as a guide by sliding tracheotomy tube (432) over hollow needle (442) as tracheotomy tube (432) is inserted into the patient's neck. As shown in FIG. 3B, to allow hollow needle (442) to serve as a guide for tracheotomy tube (432), before the device (100, 200 is activated), hollow needle (442) may be inserted through tracheotomy tube (432). In addition, first mechanical arm (440) and/or first motor (444) may be attached to second mechanical arm (430) and or second motor (434).

Figure 3C:
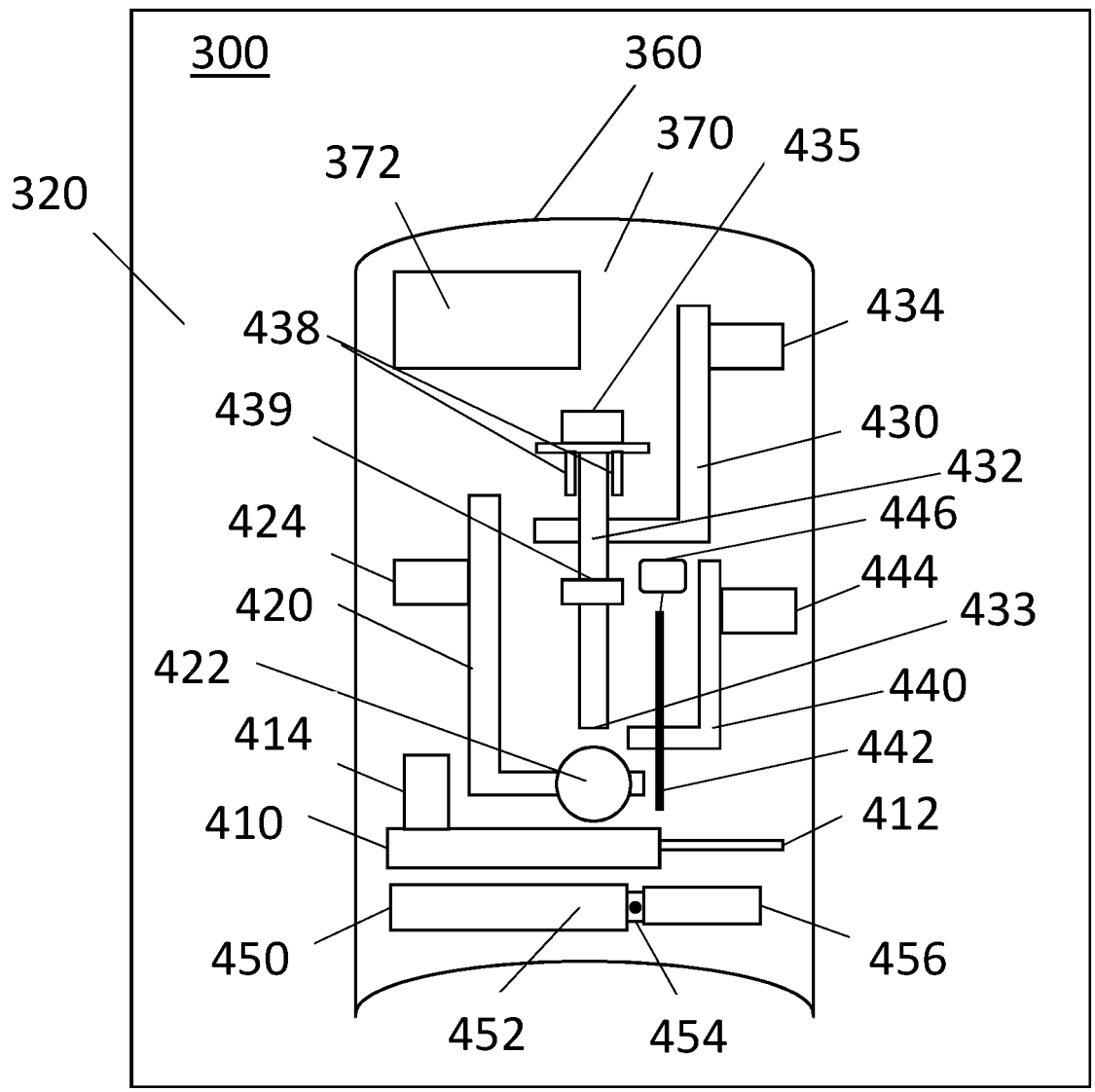
FIG. 3C depicts an interior region of an exemplary device in accordance with the present invention.

Alternatively, an incision may be made in the patient's neck before tracheotomy tube (442) is inserted. Referring to FIG. 3C, a third mechanical arm (410) and a blade (412) attached to third mechanical arm (410) may be located within interior region (370). Blade (412) may be shaped like a scalpel blade or may have another shape, such as a circular blade. Attached to third mechanical arm (410) may be a third motor (414). Third motor (414) may be powered by power source (372) and configured to move third mechanical arm (410). A third driver (not shown) may be attached to third motor (414) and configured to drive third motor (414). Device (100, 200) may be configured to extend blade (412) through aperture (160, 260), outside housing (110, 210), and toward the patient's neck, creating an incision in the patient's neck. Device (100, 200) may be further configured to move blade (412) away from the location of the incision and/or retract the blade into interior region (370) after the incision is made. Device (100, 200) may be further configured to insert first end (433) of tracheotomy tube (432) into the incision made by blade (412) after the incision is made.

Referring again to FIG. 3C, also within interior region (370) may be a fourth mechanical arm (420), a dilating tool (422) attached to the fourth mechanical arm (420), a fourth motor (424) powered by the power source (372) and configured to move fourth mechanical arm (420), and a fourth driver (not shown) configured to drive the fourth motor (424). Dilating tool (422) may be used to expand the incision to facilitate inserting tracheotomy tube (432) in to the patient's airway.

Figure 4A:
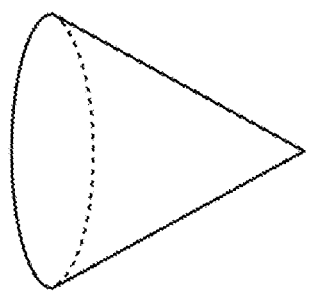
FIG. 4A depicts a tool in accordance with the present invention.
Figure 4B:
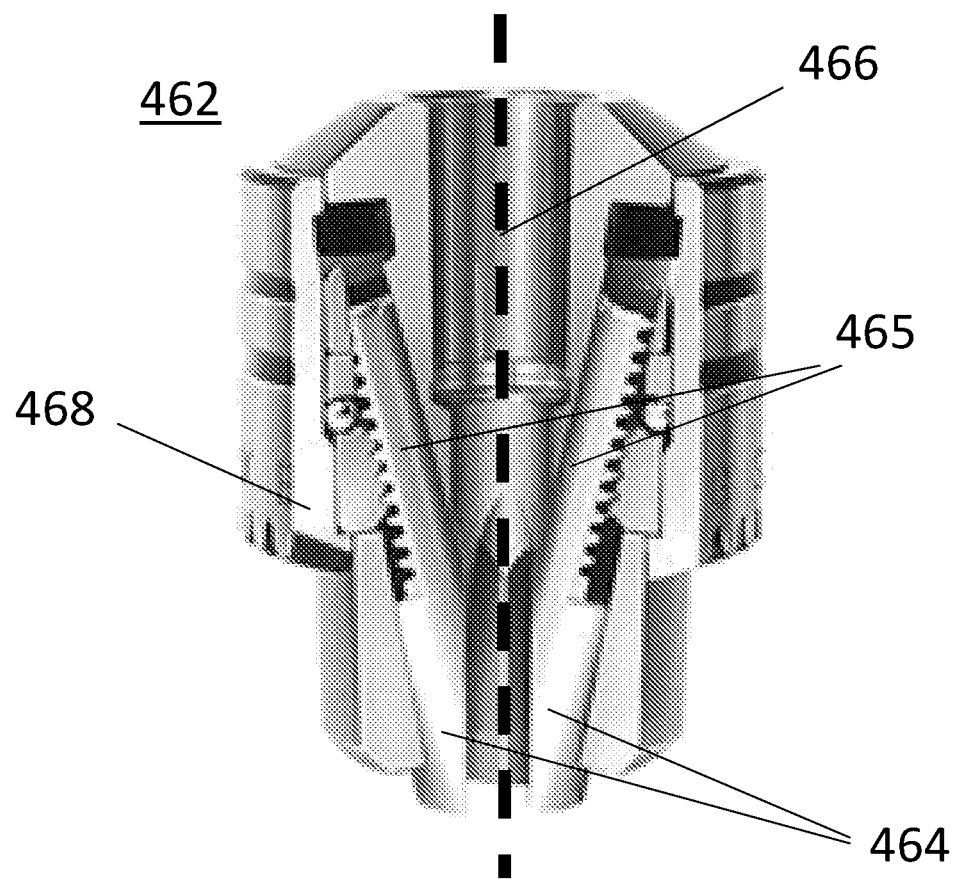
FIG. 4B depicts a tool in accordance with the present invention.

As shown in FIG. 4A, dilating tool (422) may, for example, have the shape of a cone. Alternatively, the dilating tool may have a structure and operate in a manner similar to a chuck on a power drill. For example, as shown in FIG. 4B, dilating tool (462) may have a plurality of jaws (464) that may be arranged around central axis (466). An upper portion (465) of each jaw (464) may be threaded and may be angled away from central axis (466). A sleeve (468) may surround all or part of jaws (464). Rotating sleeve (468) may cause threads located therein to slide relative to the threaded portion of each jaw (464), causing the jaws to move toward or away from central axis (466).

To dilate an incision made by blade (412), device (100, 200) may be configured to extend dilating tool (422, 462) through aperture (160, 260), outside housing (110, 210), and toward the incision. If dilating tool (422) is shaped like a cone, the tip of the cone may be inserted into the incision. As dilating tool (422) is pushed further into the incision, the incision may be expanded. If dilating tool (462) has jaws (464) similar to a power drill chuck, the jaws (464) may be inserted into the incision created by blade (412), and then jaws (464) may be separated to dilate the incision. Device (100, 200) may be further configured to move the dilating tool (422, 462) away from the incision and/or retract dilating tool (422, 462) into interior region (370) after the incision is dilated.

Each dilating tool may be capable of cauterizing the incision to inhibit blood from flowing from the incision into the airway. For example, the dilating tool may be connected to the power source. As the dilating tool is inserted into the incision, an electric charge sufficient to cauterize the incision may be delivered from the power source to the outer surface of the dilating tool. The electric charge may be delivered multiple times, and may be delivered at predetermined distance intervals as the dilating tool is inserted into the incision. For example, an electric charge may be applied each time the dilating tool is inserted an additional two millimeters. Similarly, an electrical charge may be applied to the tracheotomy tube.

Device (100, 200) may include separate mechanical arms to deploy each of the tools used for the tracheotomy procedure, e.g., the hollow needle, the blade, the dilating tool, and the tracheotomy tube. Alternatively, one or more of the tools may be stored within the interior region of the device. One or more mechanical arms may deploy a plurality of tools by employing a first tool, detaching from the first tool (e.g. by storing the tool in the device), attaching to a second tool, and deploying the second tool. In that way, a single mechanical arm may be used to deploy two, three, or all of the tools. For example, a single mechanical arm attached to a blade may be moved so as to use the blade to make an incision in a patient's neck, may disengage from the blade and attach to a dilating tool, may position the dilating tool so as to cause the incision to be dilated, may disengage from the dilating tool and attached to a tracheotomy tube and may insert the tracheotomy tube through the incision.

Figure 5A:
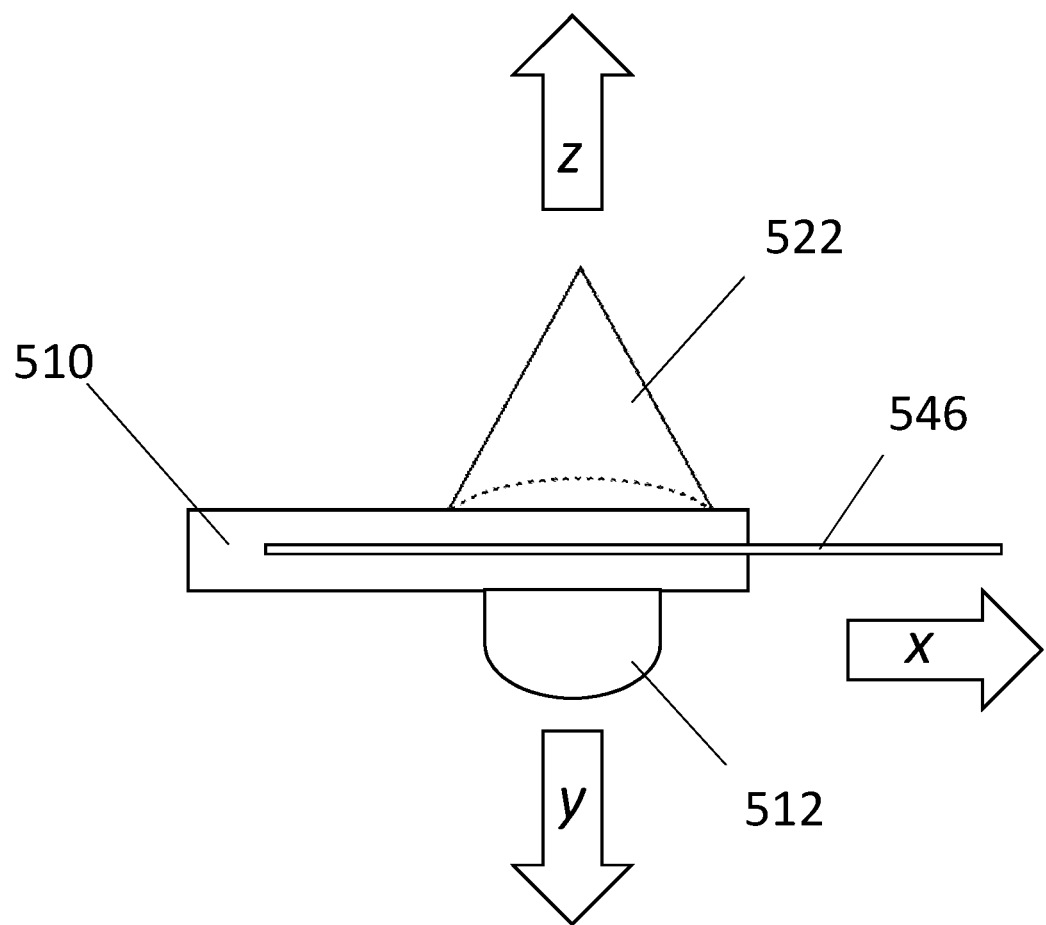
FIG. 5A depicts a mechanical arm and tools attached thereto in accordance with the present invention.

Alternatively a plurality of the tools used to perform the procedure may be attached to one arm. For example, as shown in FIG. 5A, blade (512), dilating tool (522), and/or hollow needle (546) may be attached to the same mechanical arm (510). Once device (100, 200) is positioned on a patient's neck—which may include aligning the curvature of the front wall (120) or indentation (222) with the front of a patient's neck, using a scanner to detect an airway and/or using a hollow needle to detect a change in air pressure as discussed above—mechanical arm (510) may be rotated to orient and use each tool in sequence to perform the tracheotomy procedure. For example, mechanical arm (510) may be oriented first so that direction "x" is toward the patient's neck to insert hollow needle (546) into the patient's neck. Mechanical arm (510) may then be oriented so that direction (y) is toward the patient's neck so that blade (512) may be used to make an incision. Mechanical arm (510) may then be oriented so that direction (z) is toward the patient's neck so dilating tool (522) may be used to dilate the incision.

Figure 5B:
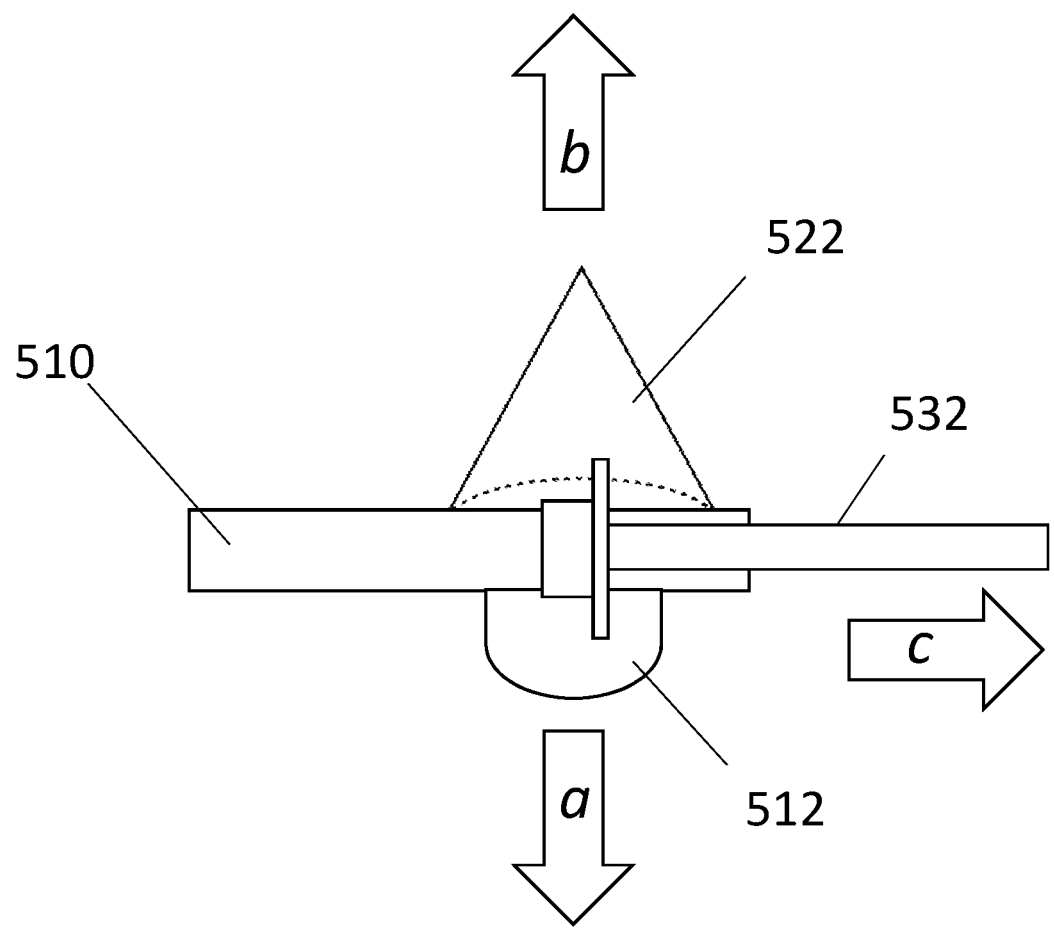
FIG. 5B depicts a mechanical arm and tools attached thereto in accordance with the present invention.

Alternatively, as shown in FIG. 5B, blade (512), dilating tool (522), and/or tracheotomy tube (532) may be attached to the same mechanical arm (510). Once device (100, 200) is positioned on a patient's neck, mechanical arm (510) may be rotated to orient and use each tool in sequence to perform the tracheotomy procedure. For example, mechanical arm (510) may be oriented first so that direction "a" is toward the patient's neck so that blade (512) may be used to make an incision. Mechanical arm (510) may then be oriented so that direction (b) is toward the patient's neck so dilating tool (522) may be used to dilate the incision. Mechanical arm (510) may then be oriented so that direction (c) is toward the patient's neck so the tracheotomy tube may be inserted into the incision.

Figure 5C:
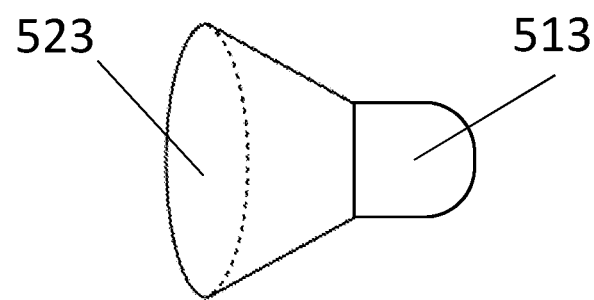
FIG. 5C depicts tools in accordance with the present invention.

A device in accordance with the present invention may also combine one or more of the tools described above, including the blade, dilating tool, hollow needle, and/or tracheotomy tube. For example, as shown in FIG. 5C, the blade (513) and dilating tool (523) may be combined into a single tool. Blade (513) may then be used to make an incision, and blade (513) may be extended into the incision so that dilating tool (523) may dilate the incision.

Figure 5D:
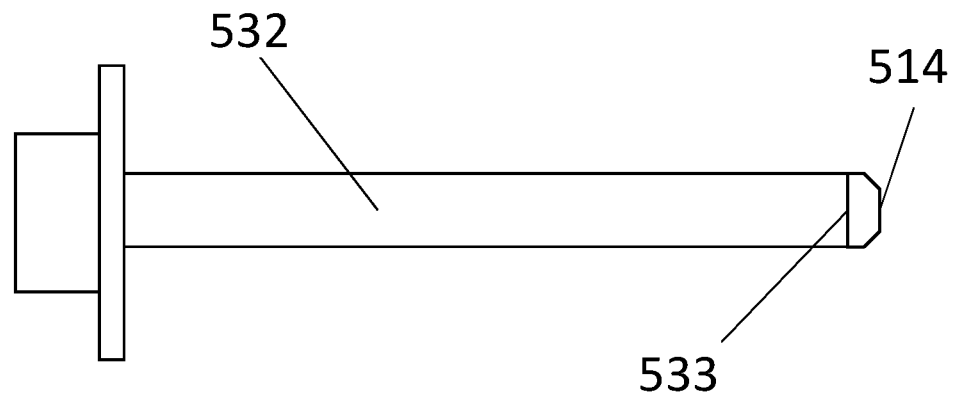
FIG. 5D depicts a tracheotomy tube in accordance with the present invention.

Alternatively, as shown in FIG. 5D, a cutting edge (514) may be included at the leading edge (533) of a tracheotomy tube (532). Once device (100, 200) is positioned on a patient's neck, cutting edge (514) may be used to make an incision, and then leading edge (533) of tracheotomy tube (532) may be inserted into the patient's airway. Alternatively or additionally, leading edge of tracheotomy tube (532) may be tapered to facilitate insertion of tracheotomy tube (532) without using a separate dilating tool. If tracheotomy tube (532) is sufficiently tapered, leading edge (533) of tracheotomy tube may be inserted into the patient's throat without first using cutting edge (514) or a blade to make an incision.

Also within interior region (370) may be a vessel (450) having an internal chamber (452) and a dispensing nozzle (454). Attached to dispensing nozzle (454) and electronically connected to one or more controllers may be an actuator (456). Actuator may be capable of activating (e.g., depressing) dispensing nozzle (454) upon receiving a signal from the one or more controllers. Located within internal chamber (452) of vessel (450) may be a topical anesthetic and/or a disinfectant. Before an incision is made by blade (412), a signal may be sent from the one or more controllers to actuator (456), causing the dispensing nozzle (454) to dispense the contents of vessel (450). Dispensing a disinfectant may help prevent an infection. Dispensing an anesthetic may help alleviate the pain cause by the incision.

Figure 6A:
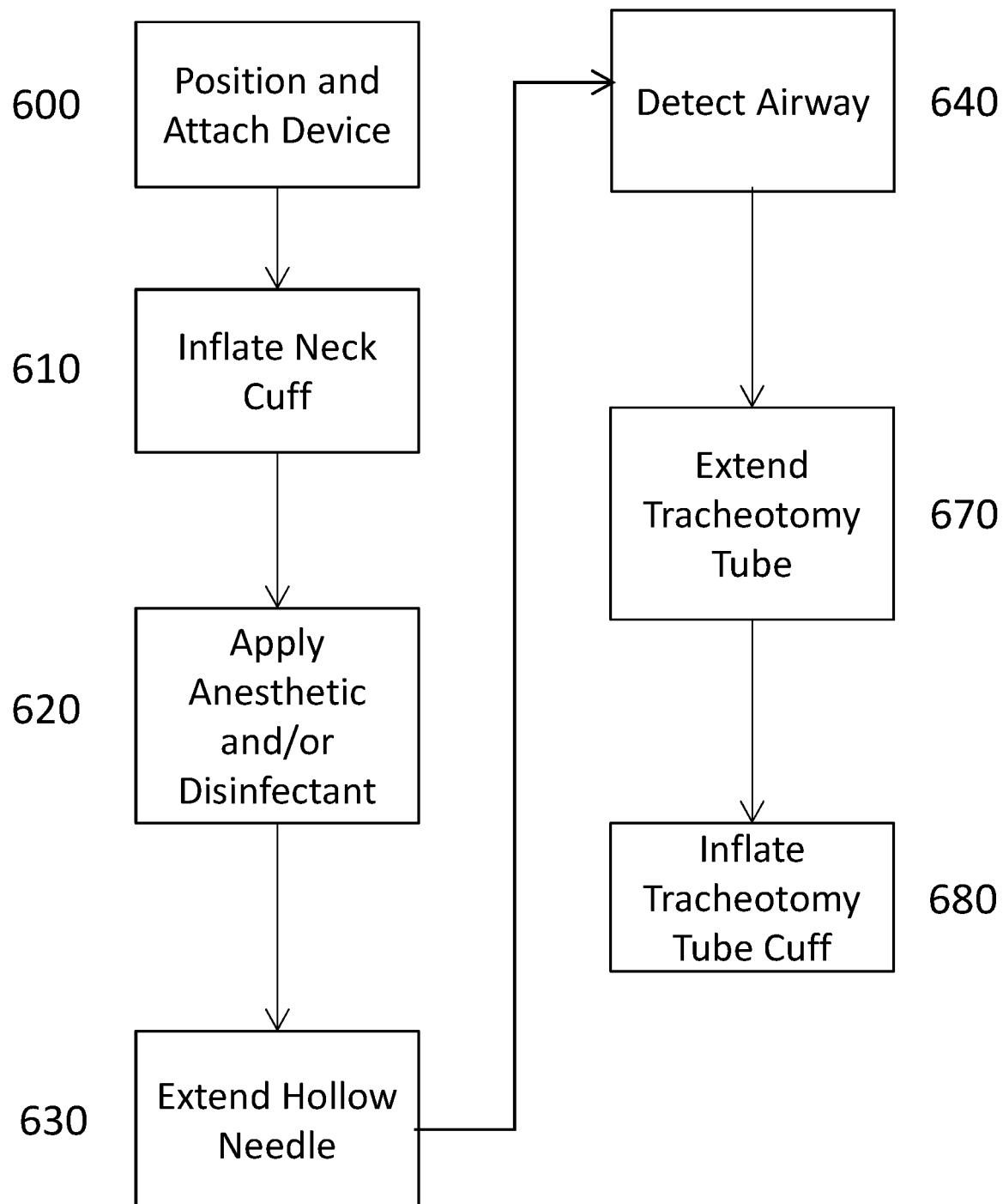
FIG. 6A is a flowchart depicting operation of an exemplary device in accordance with the present invention.

FIG. 6A is a flowchart depicting an exemplary sequence of operations for a device in accordance with the present invention. The sequence of operations may be initiated by, for example, depressing a button (155, 255) on the device. At Step (600), the device may be positioned on the neck of the person on whom the tracheotomy procedure is to be performed ("the patient"). Front wall of the housing of the device may be curved or may have a curved indentation that matches or is similar to the contour of a person's neck. One or more straps may be used to secure the device to the patient's neck. The straps may have airtight chambers that may be inflated to secure the device to the patient's neck and/or to immobilize the patient's neck.

At Step (610), the airtight chambers may be inflated by, for example, injecting air into the airtight chambers from an air canister that may be located outside the housing of the device, or inside the housing of the device. Alternative, the airtight chambers may be inflated by a chemical reaction between two chemicals. One chemical may be located within the airtight chamber, and a second chemical may be located within a packet inside the airtight chamber. When the packet is broken, the chemicals may contact each other, generating a gas.

At Step (620), a signal may be sent to an actuator within the device causing the contents of a vessel within the device to be applied to the neck of the patient. The contents of the vessel may include an anesthetic and/or a disinfectant.

At Step (630), the open tip of a hollow needle may be extended outside the housing of the device at a first location. At Step (640), an air pressure sensor in fluid communication with the interior of the hollow needle may be used to detect a change in air pressure indicating whether air is flowing into needle from the open tip of the needle. A change in air pressure above a predetermined amount or predetermined percentage or within a predetermined range may indicate that the open tip of the hollow needle has reached the patient's airway. Regardless of whether the flow of air is detected by the air pressure sensor, the method may proceed to Step (670).

Alternatively, if a change in air pressure above a predetermined amount is not detected by the air pressure sensor, indicating that the open tip of the hollow needle did not reach the patient's airway, the open tip of the hollow needle may be retracted and extended from the housing of the device at a second location. For example, the second location may be one centimeter to the left, right, above, or below the first location. If a change in air pressure is not detected at the second location, the open tip of the hollow needle may be shifted again to a different location that is at a predetermined distance and orientation from the second location. Repositioning of the needle may continue until a change in air pressure above a predetermined amount or percentage or within a predetermined range is detected.

At Step (670), a tracheotomy tube may be extended outside the housing. The tracheotomy tube may be extended with sufficient force to pierce the patient's neck and extend into the patient's airway. The tracheotomy tube may be inserted around the hollow needle, thereby using the hollow needle as a guide.

At Step (680) a cuff on the tracheotomy tube may be inflated. Additionally or alternatively, flanges on the tracheotomy tube may be extended to help ensure that the tracheotomy tube remains in place.

Figure 6B:
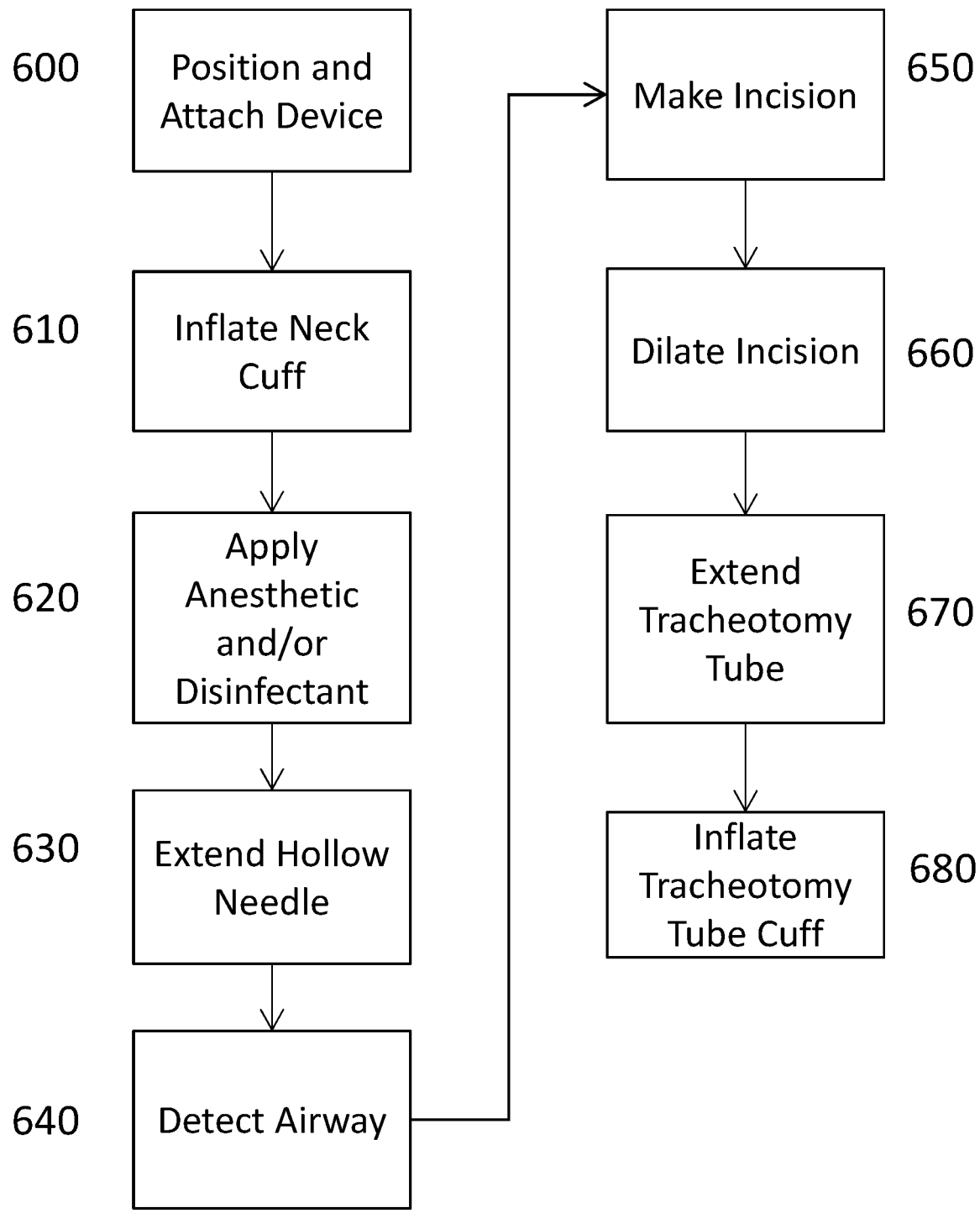
FIG. 6B is a flowchart depicting operation of an exemplary device in accordance with the present invention.

Referring to FIG. 6B, as an alternative method, an insertion may be made, and the insertion may be dilated before the tracheotomy tube is inserted. For example, Steps (600), (610), (620), (630), (640), (670), and (680) may be the same as described above. But immediately following Step (640), at Step (650) a blade may be extended from the housing, toward the patient's neck to make an incision. At Step (660), a dilating tool may be extended from the housing to the location where the insertion was made and used to dilate the incision. Then at Step (670), a tracheotomy tube may be inserted into the dilated incision.

At Step (680) a cuff on the tracheotomy tube may be inflated. Additionally or alternatively, flanges on the tracheotomy tube may be extended to help ensure that the tracheotomy tube remains in place.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A method of operating a portable device capable of performing a tracheotomy procedure on a patient, said portable device having a power source; a tracheotomy tube; a hollow needle and an air pressure sensor attached to said hollow needle; a non-transitory memory having a machine-readable medium comprising machine executable code; and a controller coupled to the memory, said method comprising the steps of:

placing the portable device adjacent to the front of a patient's neck;

activating the portable device, thereby causing the portable device to, without further intervention from a user of the device, perform the steps of:

determining a location of the patient's airway;

creating an incision in the patient's neck;

inserting at least a portion of the tracheotomy tube through the incision, into the patient's airway.

2. The method of claim 1, further comprising attaching the portable device to the patient's neck.

3. The method of 2, wherein the step of determining the location of the patient's airway comprises inserting the hollow needle into the patient's neck at a first location, and using data received from the air pressure sensor to determine a change in air pressure in the hollow needle.

4. The method of claim 3, further comprising determining from the data received from the air pressure sensor whether the air pressure in the hollow needle has changed a predetermined amount.

5. The method of claim 4, further comprising moving the needle to a second location.

6. The method of claim 1, wherein the step of determining the location of the patient's airway comprises inserting the hollow needle into the patient's neck at a first location, and using data received from the air pressure sensor to determine a change in air pressure in the hollow needle.

7. The method of claim 6, further comprising determining from the data received from the air pressure sensor whether the air pressure in the hollow needle has changed a predetermined amount.

8. The method of claim 7, further comprising moving the needle to a second location.

9. A method of operating a portable device capable of performing a tracheotomy procedure on a patient, said portable device having a power source; a tracheotomy tube; a non-transitory memory having a machine-readable medium comprising machine executable code; and a controller coupled to the memory, said method comprising the steps of:

placing the portable device adjacent to the front of a patient's neck;

attaching the portable device to the patient's neck;

activating the portable device, thereby causing the portable device to, without further intervention from a user of the device, insert at least a portion of the tracheotomy tube into the patient's airway without any incision having previously been made in the patient's neck at a location where the tracheotomy tube is inserted.

10. The method of claim 9, wherein the portable device further comprises a hollow needle and an air pressure sensor attached to said hollow needle.

11. The method of claim 10, wherein a step of determining a location of the patient's airway comprises inserting the hollow needle into the patient's neck at a first location, and using data received from the air pressure sensor to determine a change in air pressure in the hollow needle.

12. The method of claim 11, further comprising determining from the data received from the air pressure sensor whether the air pressure in the hollow needle has changed a predetermined amount.

13. The method of claim 12, further comprising moving the needle to a second location.

14. The method of claim 9, wherein the portable device further comprises a hollow needle and an air pressure sensor attached to said hollow needle.

15. The method of claim 14, wherein a step of determining a location of the patient's airway comprises inserting the hollow needle into the patient's neck at a first location, and using data received from the air pressure sensor to determine a change in air pressure in the hollow needle.

16. The method of claim 15, further comprising determining from the data received from the air pressure sensor whether the air pressure in the hollow needle has changed a predetermined amount.

17. The method of claim 16, further comprising moving the needle to a second location.

* * * * *